United States Patent [19]
Usala

[11] Patent Number: 5,922,339
[45] Date of Patent: Jul. 13, 1999

[54] COMPOSITIONS AND METHODS FOR BIOCOMPATIBLE IMPLANTS

[76] Inventor: Anton-Lewis Usala, 237 Buckingham Dr., Winterville, N.C. 27890

[21] Appl. No.: 09/013,750

[22] Filed: Jan. 27, 1998

[51] Int. Cl.⁶ .............................. A61F 2/02; A61K 47/30
[52] U.S. Cl. ............................................................ 424/424
[58] Field of Search .......................... 424/424; 514/772.3

[56] References Cited

U.S. PATENT DOCUMENTS

| | | | |
|---|---|---|---|
| 4,340,458 | 7/1982 | Lerner et al. | 204/195 R |
| 4,788,271 | 11/1988 | Hergenrother et al. | 528/125 |
| 4,794,090 | 12/1988 | Parham et al. | 436/531 |
| 4,797,213 | 1/1989 | Parisius et al. | 210/651 |
| 4,868,121 | 9/1989 | Scharp et al. | 435/268 |
| 5,079,160 | 1/1992 | Lacy et al. | 435/240.2 |
| 5,151,183 | 9/1992 | Sedath et al. | 210/500.41 |
| 5,322,790 | 6/1994 | Scharp et al. | 435/268 |
| 5,614,205 | 3/1997 | Usala | 424/424 |

FOREIGN PATENT DOCUMENTS

| | | |
|---|---|---|
| 0 138 150 | 4/1985 | European Pat. Off. . |
| 0 259 109 | 3/1988 | European Pat. Off. . |
| WO 92/10584 | 6/1992 | WIPO . |
| WO 92/19195 | 11/1992 | WIPO . |
| WO 93/13408 | 7/1993 | WIPO . |
| WO 93/16685 | 9/1993 | WIPO . |
| WO 94/16002 | 7/1994 | WIPO . |
| WO 95/19430 | 7/1995 | WIPO . |

OTHER PUBLICATIONS

David A. Gough et al., Progress Toward a Potentially Implantable, Enzyme–Based Glucose Sensor, *Diabetes Care*, vol. 5 No. 3, May–Jun. 1982.

P. Metrakos et al., Collagen Ge. Matrix Promotes Islet Cell Proliferation, Transplantation Proceeds 26(6):3349–3350 (1994).

David A. Gough et al., Development of the Implantable Glucose Sensor, *Diabetes*, vol. 44, Sep. 1995.

Centonze et al., "Permeation of Solutes Through an Electropolymerized Ultrathin Poly–o–Phenylenediamine Film Used as an Enzyme–Entrapping Membrane", *Electronanalysis* 6:423–429 (1994).

*Primary Examiner*—Carlos A. Azpuru
*Attorney, Agent, or Firm*—Alston & Bird LLP

[57] ABSTRACT

Methods and compositions for preventing an immune response in a mammal having an implanted transplant are provided. The compositions comprise non-immunogenic aromatic chains with interspersing aliphatic groups. Such compositions are useful as polymer coatings that protect against immune recognition.

22 Claims, 1 Drawing Sheet

COMPOSITIONS AND METHODS FOR BIOCOMPATIBLE IMPLANTS

FIELD OF THE INVENTION

The invention relates to polymer chemistry, immunology and transplantation, particularly to the field of materials for use in conjunction with transplantation and implantation of foreign cells and biological materials.

BACKGROUND OF THE INVENTION

The replacement of damaged or diseased tissues or organs by transplantation has been and continues to be a long-standing goal of medicine towards which tremendous progress has been made. Controlling rejection while avoiding the adverse side effects of immunosuppressive agents is pivotal to successful transplantation. Rejection is characterized by perivascular infiltration of killer T-lymphocytes, which cause cellular necrosis if not checked. Since early rejection can be silent, it is important to detect it before necrosis occurs. Immunologic monitoring of activated T-lymphocytes in peripheral blood offers clues to the timing of a rejection process but has not been sufficiently reliable to dictate anti-rejection therapy.

Immunosuppressive therapy regimens vary but usually include therapy with cyclosporine, azathioprine, and prednisone. However, there are adverse side effects of these agents. Thus, careful monitoring of the side effects is extremely important. Such side effects include nephrotoxicity, bone marrow suppression, and opportunistic infections.

The most serious problem restricting the use of allografts is an immunological one. Because their cellular constituents express on their surfaces a variable number of genetically determined transplantation antigens, which are lacking in the host, allografts provoke a defensive type of reaction analogous to that incited by pathogenic microorganisms. As a consequence, after a transient initial period of apparent well being, there is often a functional deterioration in the graft associated with its progressive destruction. The host response, known as the allograft rejection, is expressed by the generation of a variety of putative immunological effectors, including cytotoxic antibodies and effector lymphocytes of various types. The destructive process varies somewhat according to the type of allograft involved as well as the degree of antigenic disparity between donor and recipient; for example, hyperacute rejection of kidneys is mediated by antibodies whereas acute rejection is a lymphocyte-mediated process.

Therefore, mammalian systems recognize foreign materials such as bacteria, viruses, penetrating or surgically implanted objects, or xenograft tissue. Upon binding to sites on these foreign entities, the cascade of events occurs that notify immune cells to surround such material and release cytotoxic materials as well as stimulate fibrin deposition to isolate the material.

Nearly all binding of cell surfaces occurs not through covalent or ionic bond formation, but through dipole moment attraction and hydrogen bond formation. As opposed to ionic or covalent bond formation, dipole moment and hydrogen bond formation require comparatively little energy. Upon close proximity to oppositely charged moieties, or electron donor and electron accepting atoms, such attractive forces are sufficient to allow proteins on cell surfaces to interact. By preventing such interactions from occurring, immune cells such as lymphocytes, macrophages, or neutrophils cannot bind to foreign materials. Without such binding, the materials are not recognized as foreign. Connective tissue protein such as fibrin forms initial attachment by binding positively charged (electron accepting) atoms to negatively charged (electron donating) oxygen atoms of the carbonyl groups. This provides the means of isolating foreign substances by dipole moment or hydrogen bonding interaction.

All proteins have electron accepting amine groups and electron donating carbonyl groups as part of each amino acid. Thus, polymer coatings that have electron accepting groups (amine, hydrogen, or other cationic species) will form attachments to both the cell surface and connective tissue protein carbonyl groups. Polymer coatings such as acrylates, polyesters, polyethylene glycol, polyvinilidine fluoride that contain exposed groups with a negative moment such as halogens or oxygen, attract the positive amine groups of proteins in cell surfaces. Likewise, polymer coatings that contain positively charged groups such as polyamides, attract the negative polar moment of halogens, oxygens, sulfone, sulfate and other groups.

Accordingly, there is needed a polymer coating which will not evoke the immune response for transplantation and other uses.

SUMMARY OF THE INVENTION

Compositions and methods for preventing an immune response in a mammal to a transplant are provided. The compositions comprise non-immunogenic, non-binding aromatic chains with interspersing aliphatic groups. The compositions are useful as polymer coatings that prevent immune recognition or binding of endogenous proteins. The compositions are useful as coatings for artificial organs and other transplants including both living and nonliving tissue.

DETAILED DESCRIPTION OF THE INVENTION

Figure 1A:
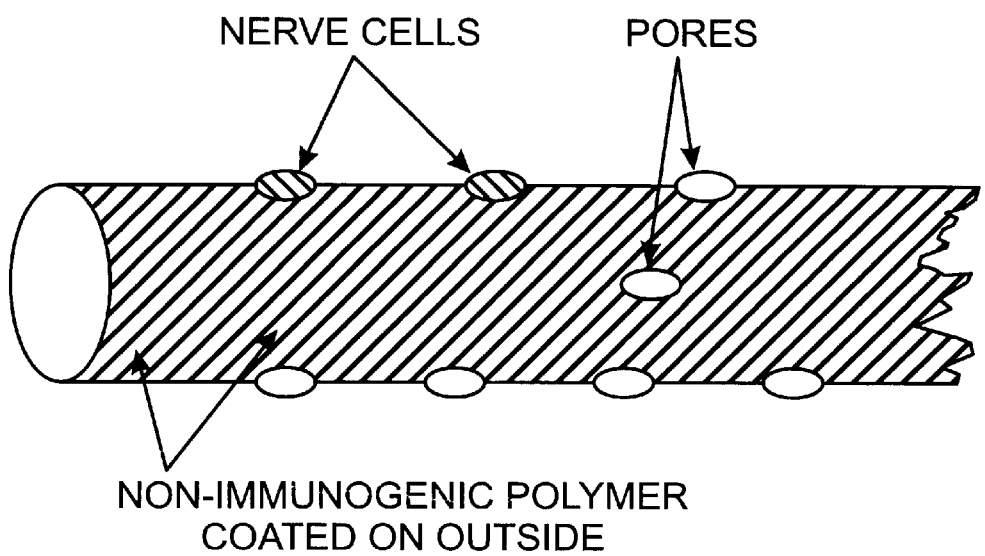
FIG. 1A provides a said view of a bioartificial nerve coated with the polymer.

Compositions comprising chemical structures that can be used to prevent protein binding and immune cell recognition as part of a transplant are provided as well as methods for making and utilizing the chemical structure. The chemical structures comprise non-immunogenic aromatic chains with interspersing aliphatic groups. The compositions provide a biocompatible immunoisolatory vehicle suitable for long-term implantation into mammals.

As noted, the compositions of the invention comprise non-immunogenic, non-binding polymers. The basic chemical unit involved with the polymer is the aromatic ring. The unsubstituted aromatic ring is resistant to polar binding, as there are no electrophilic or nucleophilic centers available without the use of significant energy or catalysts. The absence of polar groups attached to the aromatic ring thus precludes dipole moment interactions or hydrogen bonding of polar protein groups.

The chemical polymers of the invention comprise unsubstituted aromatic rings wherein the aromatic rings have no attached polar groups. Such aromatic groups include benzene or benzene derivatives, naphthalene or naphthalene derivatives, etc., or combinations thereof.

Examples of the chemical polymers of the invention include the general formulas:

[Structural formula: 4,4' diphenyl alkene]

[Structural formula: 3,3' diphenyl alkene]

[Structural formula: 3,4' diphenyl alkene]

Wherein M is any aliphatic group such as $CH_2$, $C_nH_{2n}CH=CH$, $C(CH_3)_2$, etc., CO, NH, SH etc. and combinations thereof;

and n and n' are positive integers. Preferably n is about 1 to about 8.

The value of n' may vary depending on the size or length of the polymeric molecule.

It is also recognized that naphthalene derivatives may be utilized in the methods of the invention. Such polymers comprise the general formula:

[Structural formulas of naphthalene derivatives]

Where M is any aliphatic group such as $CH_2$, $C_nH_{2n}$, $CH=CH$, $C(CH_3)_2$, etc., CO, NH, SH etc. and combinations thereof;

and n and n' are positive integers, where n is preferably about 1 to about 8.

As noted above, n' may vary depending on the size of the polymer.

It is recognized that various combinations, modifications and linkages of the derivative backbones may be used. For example, the polymer may comprise mixtures of benzene and naphthalene derivatives. The examples above are merely provided for illustration. Such modifications and combinations are encompassed by the present invention.

U.S. Pat. No. 5,614,205 provides a polymeric material of poly-para-xylylene. The patent, assigned to Encelle is drawn to a bioartificial pancreas which is encapsulated within a polymeric material selected from poly-para-xylylene, poly-monochloro-xylylene, and poly-dichloro-xylylene. Accordingly, the present genus of encapsulating polymeric materials excludes poly-para-xylylene, poly-monochloro-xylylene, and poly-dichloro-xylylene. It is submitted that from the teachings of the U.S. Pat. No. 5,614,205, one would not have known the basis for the immune-protective characteristics of the polymer coating. The present invention recognizes that the protective characteristics are not limited to the polymers set forth in the U.S. Pat. No. 5,614,205 but describe generic formulas for constructing chemical polymers which can be used to prevent protein binding and immune cell recognition. It was not until the present invention that the mechanisms underlying the protective coating have been elucidated.

It is now recognized that the unsubstituted aromatic ring is resistant to polar binding and thus provides a protective coating for use in transplants. The polymer prevents the passage of immunogenic agents. The absence of polar groups on the aromatic ring prevents immune recognition or biofouling of substrates encased in such polymers. That is, the polymer coatings of the invention prevent biological overgrowth and fouling. Such polymer membranes of the invention are biocompatible in that they do not elicit an inflammatory response in the host.

The biological coating or membrane of the invention is characterized by a phenyl-based polymer. The phenyl groups of the polymer have interspersing aliphatic groups. Such aliphatic groups include, but are not limited to members of carbon based substitutions, $CH_2$, $C_nH_{2n}$, $CH=CH$, $C(CH_3)_2$ and the like, CO, as well as NH, SH, etc. and any combinations thereof. It is recognized that the carbon based substitutions may be preferred because of its extremely low polar charge. Therefore, such embodiments avoid immune recognition or protein binding after implantation. The resulting polymer comprises aromatic rings that provide protection from host binding while the interspersing aliphatic groups provide binding to existing structures; such as, for example, an outer coating.

The polymer coatings of the invention provide a semipermeable membrane or surrounding surface to protect cellular moieties and other transplants from the patient or mammalian immune system while allowing cell nutrients, chemical signals for the cellular production, and the chemical moiety produced thereby to flow through the membrane.

Chemical moieties include hormones, cell nutrients, pharmaceuticals, and the like.

The porosity of the membrane can vary. To increase the area between polymer chains, and thereby provide porosity for larger molecules, aliphatic connectors of decreased polarity and/or similar charge can be utilized such as $CH_2$. In the same manner, by increasing the number of aliphatic groups that connect the phenyl rings, the polymer provides increasing sites for binding to an underlying structure, but decreases the protection from fibrous protein attachments. It is further recognized that increasing the number of aliphatic connecting groups will increase the flexibility of the polymer coating by allowing more freedom of rotation to the aromatic rings. For purposes of the present invention, any combination of aliphatic group connectors can be utilized. That is, the connector or linkage between the aromatic moieties may comprise the same aliphatic group or any arrangement of groups.

The maximum pore size is selected to prevent passage of immunoglobulins and antibodies having molecular weights of about 40,000 to about 500,000. The minimum pore size, as noted, is selected to permit the passage of chemical moieties of interest as well as nutrient molecules. Thus, the minimum pore size may vary depending on the molecular weight of the moiety being released.

As noted above the length of the connector (M) is related to porosity and flexibility of the membrane. Generally, the connector will comprise from about one to about eight aliphatic groups, preferably about one to about five aliphatic groups, more preferably about one to about four aliphatic groups. It is recognized that the polymer membranes of the invention will have a porosity that permits passage therethrough of effective nutrients for the cellular moiety or transplant and for the hormone, peptide, enzyme, protein, and the like produced by the transplant.

The 3,3'diphenyl alkene derivative stoichiometrically may provide the greatest protection from protein binding. However, both the 3,4'diphenyl alkene and the 4,4'diphenyl alkene as well as derivatives thereof provide adequate protection from immune recognition.

The thickness of the polymers of the invention can be controlled to about 5 to about 10 Angstroms using vacuum deposition. Dimers of the aromatic backbone polymers can be pyrolized, then vaporized, and finally deposited on structures or transplants within a vacuum chamber. The thickness of the deposition can be altered for any of the aromatic polymers by length of time in the vacuum. As such, the thickness of the resultant polymer can be controlled to allow passage of moieties based on their molecular weight thickness and to exclude other moieties.

Membranes having a thickness of about 100 to about 7500 Angstroms preferably about 1500 to about 5000 Angstroms, and more preferably about 2500 to about 3500 Angstroms, provide the desired porosity characteristics for bioartificial organs.

Non-living tissue or structures, such as a microporous carrier, may be coated with from about 50 to about 500, preferably from about 100 to about 200 Angstroms of coating material to prevent fibrous attachment to fibrous attachment to the non-polar aromatic polymers described herein. Any material inside the coated porous carrier can diffuse into a host body into which the carrier has been implanted. In the same manner, materials or substances from the host may diffuse into the implanted carrier. It is recognized that the lower limit may be much below that given above as long as the thickness does not result in insufficient membrane strength. The thickness of the membrane coating may vary, but as long as it is sufficiently thick to prevent direct contact between the cells and/or substances on either side of the membrane barrier. The thickness of the membrane generally ranges between about 4 to about 200 microns; preferably about 10 to about 100 microns more preferably about 5 to about 50 microns.

It is further recognized that in instances where the transfer or diffusion of materials is not desired, thicker coatings may be applied. Coating with thicknesses of greater than about 2000 Angstroms would effectively prevent any transfer of materials of approximately 20,000 to about 60,000 mw through the polymeric coating but would prevent materials from adhering to coated structure. Thus, the aromatic fibers could be used on structures, tubing, devices, etc. for implantation where it is desired to avoid fibrous attachment or cells from adhering. Such structures include stents such as coronary artery stents, vascular grafts, catheters such as central venous or arterial catheters, dialysis shunts, intravenous catheters, or other structural supports.

Types of immunological attack which can be prevented and are minimized by the use of the polymer coatings of the invention include attack by microphages, neutrophils, cellular immune responses (e.g., natural killer cells and antibody-dependent T cell-mediated cytolysis), and humoral response (e.g., antibody-dependent compliment mediated cytolysis).

Methods for formation of the membranes and deposition on a transplant are available in the art. See, for example, U.S. Patent No. 5,614,205, herein incorporated by reference. Generally, the membranes are formed by conventional vacuum deposition and have a porosity which can be accurately controlled such that a selective membrane may be established. As mentioned above, the aromatic coating may be applied using conventional equipment available from Specialty Coatings System of Indianapolis, Indiana or Para Tech Coating, Inc. of Aliso Viejo, Calif., who also supply the aromatic chain structure. The equipment is available in various configurations which can apply a coating to exacting specifications.

One particular machine configuration is set forth in U.S. Pat. No. 4,683,143 issued to Riley. Basically, all such systems use a vaporizer connected to a pyrolizer that is in turn connected to a vacuum chamber evacuated by a cold trap protected by vacuum pump. Under vacuum and heat, the aromatic structure is vaporized in the vaporizer and passes to the pyrolizer wherein the chain is thermally cleaved to a monomer which is conformally deposited on the devices in the chamber, at ambient temperature, as a long chain polymer. As is well known the thickness of the coating on coated parts may be determined by locating a planar witness plate in the coater during the coating process. Inasmuch as the entire chamber, fixture and parts receive a substantially uniform coating, the witness plate may be removed and tested by conventional thickness measuring apparatus to thereby determine the thickness on the coated part. This is a convenient procedure for preformed films, as described in some of the embodiments below. However, when the coating is applied over a hydrogel matrix as described in other embodiments below, it is noticed that cooling of the matrix occurs due to outgassing of liquids, resulting in variations in the thickness between the witness plate and the applied membrane as visually observable on the basis of color variations therebetween, the paralene having a distinctive coloration spectrum versus thickness. At the present time, Applicant is not aware of available thickness measuring equipment for providing direct measurement of membrane thickness under these conditions. Nonetheless, the specific attributes of the membrane devices in accordance with the present invention may be determined by functional in vitro testing as supplemented by the basic parameter requirements as noted below.

In the present invention, the maximum pore size is selected to prevent passage of immunoglobulins and antibodies having molecular weights of 40,000 to about 500,000. The minimum pore size is selected to permit the passage of nutrient molecules, such as glucose, electrolytes and water into and out of the transplants as well as for the release of the biological product of interest out of the device. Therefore, the aforementioned maximum porosity, as those skilled in the art will understand, would be dependent on the biological product released. For example, a bioartificial pancreatic device would require molecular weight cut off of at least 5,600 to allow passage of insulin, a device for treatment of Parkinson's disease containing substantia migra cells isolated from brain tissue would require molecular weight cut off of at least 1000 to allow passage of dopamine and related compounds, whereas treatment of hypothyroidism treated by isolated thyroid tissue would require a molecular weight cut off of only 500 to allow transfer of thyroid hormone. Thus, pore size will be set based upon the use of the transplant and the biological product to be released.

The polymer coatings of the invention have a wide range of uses. They are useful for protecting implanted cells, tissues, or other materials from immunological attack. Likewise, the coatings find use in passivation of non-living tissue and shielding such structures from reorganization by the immune system. Furthermore, the polymer coatings are useful to deliver a wide range of cellular products, including high molecular weight products, to an individual in need thereof, and/or to provide needed metabolic functions to an individual, such as the removal of harmful substances. Products which can be delivered using the above-described membrane include a wide variety of factors normally secreted by various organs or tissues including, for example, insulin to a diabetic patient, dopamine to a patient suffering from Parkinson's disease, factor VIII to a type A hemophiliac, etc.

Accordingly, the polymer coating of the invention can be used with any transplant. By transplant is intended cells, tissues, or other living or non-living devices for transplantation into a mammal. Transplants of the invention include allografts, artificial organs, cellular transplantation and other applications for hormone producing or tissue producing implantation into deficient individuals who suffer from conditions such as diabetes, thyroid deficiency, growth hormone deficiency, congenital adrenal hyperplasia, Parkinson's disease, and the like. Likewise, the polymer coatings are useful for transplants involving therapeutic conditions benefitting from implantable delivery systems for biologically active and gene therapy products for the treatment of central nervous system diseases and other chronic disorders. More specifically, devices and matrices as described will find application in the various transplantation therapies, including without limitation cells secreting human nerve growth factors for preventing the loss of degenerating cholinergic neurons, satellite cells for myocardial regeneration, striatal brain tissue for Huntington's disease, liver cells, bone marrow cells, dopamine-rich brain tissue and cells for Parkinson's disease, cholinergic-rich nervous system for Alzheimer's disease, adrenal chromaffin cells for delivering analgesics to the central nervous system, cultured epithelium for skin grafts, and cells releasing ciliary neurotropic factor for amyotrophic lateral sclerosis, and the like. Where the transplant comprises cells for the production of hormones or other factors, the cells are contained within a capsule or chamber. See for example U.S. Pat. No. 5,614,205 which discloses a bioartificial endocrine device. Such device can be utilized to house other cells in the same manner. Such disclosure is herein incorporated by reference.

The polymer coatings of the invention render the transplant biocompatible by supplying a protective coating or surrounding membrane. By biocompatible is intended that the transplant avoids detrimental effects on the body's various protective systems and remains functional for a significant period of time. In addition to the avoidance of protective responses from the immune system, or foreign body fibrotic response, biocompatible also implies that no specific undesirable cytotoxic or systemic effects are caused by the transplant and its contents such as would interfere with the desired functioning of the transplant or its contents.

The coating also provides immunoisolation. That is, the polymer coating confers protection of the transplant from the immune system of the individual in whom the transplant is implanted by preventing harmful substances of the patient's body from entering the transplant, and by providing a physical barrier sufficient to prevent detrimental immunological contact between the isolated moiety and the individual's immune system.

Figure 1B:
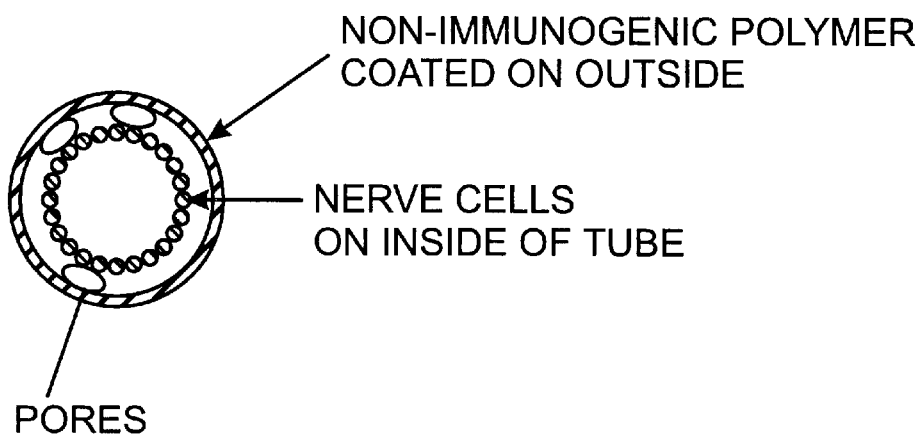
FIG. 1B provides a cross-sectional view of a bioartificial nerve coated with the polymer.

The polymer coatings of the invention may also be used in applications that require prevention of fibrous protein binding as well as required conduction of an electric signal. Such applications can be found in bio-compatible sensors, or in bio-artificial nerves. In bio-artificial nerves, a porous tube can be coated to facilitate nerve growth along the inside surface, and coated over with between about 500 to about 5,000 Angstroms of aromatic based polymer. The nerve tissue is thereby nourished by diffusion through the polymer window and can conduct its electric signal along the outside of the coated tube. See, for example, FIG. 1. This application is possible because the aromatic based polymers are unique in their ability to conduct electrical signals because of the electron cloud of the aromatic ring. The present inventor discovered that when polypara-xylylene N was coated over a porous non-conductive Delrin support, the parylene N was found by scanning electron microscopy to conduct the electron beam (appearing black) compared to the non-conducting Delrin which appears white from reflection of the beam.

EXPERIMENTAL

EXAMPLE 1

A membrane of poly-para-xylyene N having a thickness of 3,271 Angstroms was mounted on a cylindrical sleeve and partially immersed in distilled water. A liquid containing components of varying molecular weights was placed on the upper surface of the membrane. Thereafter samples of the water were applied to an SDS-PAGE gel and subjected to electrophoresis to separate the samples according to molecular weights. Low molecular weights corresponding to glucose, insulin and cell nutrients were identified. Higher molecular weight components, i.e. greater than 26,000, were excluded.

More particularly, for an implantable bioartificial pancreatic device, the cellular moiety contains a plurality of insulin producing islets. The islets are derived from donor pancreatic organs, both human and animal, in conventional manner utilizing collagenous digestion and Ficoll gradient separation. The islets are admixed with conventional RPMI culture media to form the matrix at a concentration of around 10 to 50 islets mer microliter.

The cylinder chamber may vary in size and shape for purpose of handling, coating and implantation considerations as well as the therapeutic insulin production required by the recipient.

For purposes of implant biocompatibility, the cylinder may be formed of a suitable material such as medical grade stainless steel or preferably by conformal coating with poly-para-xylyene, the thickness of which is not particularly critical, however a coating thickness of about 0.5 microns is preferred. This coating may be precisely applied in controlled thicknesses according to the conventional techniques. The coating and membrane materials are recognized as nonimmunogenic substrates for human implantation. The material does not interact with plasma factors such as fibrin or cells such as fibroblasts or platelets. Accordingly, the device and membrane pores will not become clogged or impair insulin release as a function of the host tissue growth.

EXAMPLE 2

A membrane of poly-para-xylyene N at a thickness of around 3100 Angstroms was mounted on a cylindrical sleeve and partially immersed in a media, distilled water. Seventy-five (75) adult porcine islets were placed in RPMI culture media on the top surface of the membrane. The media was periodically sampled and changed after sampling. Two aliquots were extracted from the media on the fourth and sixth days. The aliquots were tested in duplicate in an $I^{125}$Insulin RIA (Ventrex). Insulin levels on the sample from the fourth day was 70+149uU/ml and on the sample from the sixth day was 235+150 uU/ml, demonstrating that insulin secreted from the islets traversed the membrane. No fibrin or lymphaction attachment occurred.

EXAMPLE 3

A membrane of poly (m-phenylene isophthalamide), formula shown below:

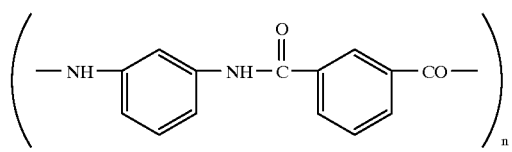

is mounted on a cylindrical sleeve and partially immersed in a media, distilled water. The membrane is applied at a thickness of about 2000 Angstroms. Seventy-five (75) adult porcine islets are placed in RPMI culture media on the top surface of the membrane. The media is periodically sampled and changed after sampling. Two aliquots are extracted from the media on the fourth and sixth days indicating insulin secretion from the islets traversed the membrane. No fibrin or lymphaction attachment is seen.

EXAMPLE 4

A membrane of poly (p-phenylene terephthalamide) the formula as given below:

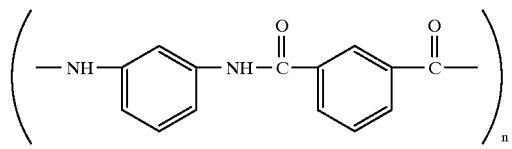

is mounted on a cylindrical sleeve and partially immersed in a media, distilled water. The membrane is applied at a thickness from about 50 to about 3500 Angstroms. Seventy-five adult porcine islets are placed in RPMI culture media on the top surface of the membrane. The membrane is periodically sampled and changed after sampling. Aliquots are extracted from the media on the fourth and sixth days and measured. Measurements indicate that insulin is secreted from the islets and traverse the membrane. No immunogenic action is seen.

EXAMPLE 5

A membrane of poly (p-phenylene terephthalamide) the formula as given below:

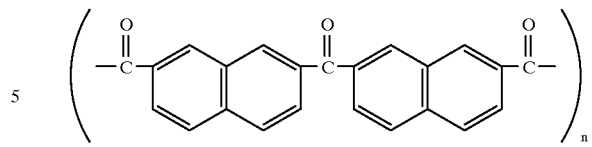

is mounted on a cylindrical sleeve and partially immersed in a media, distilled water. The membrane is applied at a thickness from about 50 to about 3500 Angstroms. Seventy-five adult porcine islets are placed in RPMI culture media on the top surface of the membrane. The membrane is periodically sampled and changed after sampling. Aliquots are extracted from the media on the fourth and sixth days and measured. Measurements indicate that insulin is secreted from the islets and traverse the membrane. No immunogenic action is seen.

EXAMPLE 6

A membrane of poly (p-phenylene terephthalamide) the formula as given below:

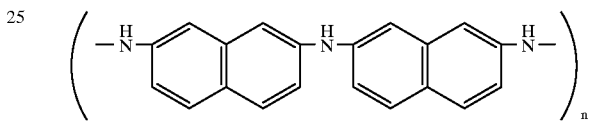

is mounted on a cylindrical sleeve and partially immersed in a media, distilled water. The membrane is applied at a thickness from about 50 to about 3500 Angstroms. Seventy-five adult porcine islets are placed in RPMI culture media on the top surface of the membrane. The membrane is periodically sampled and changed after sampling. Aliquots are extracted from the media on the fourth and sixth days and measured. Measurements indicate that insulin is secreted from the islets and traverse the membrane. No immunogenic action is seen.

The aforementioned encapsulation may be effectively utilized in other applications for hormone producing or tissue producing implantation into deficient individuals with conditions such as thyroid deficiency, growth hormone deficiency, congenital adrenal hyperplasia and the like.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A transplant which is encapsulated in a polymeric membrane, said membrane having an aromatic ring backbone with interspersing aliphatic groups wherein said membrane is not poly-para-xylylene, poly-monochloro-xylylene, and poly-dichloro-xylylene.

2. The transplant of claim 1, wherein said polymeric membrane comprises a structure selected from the group consisting of:

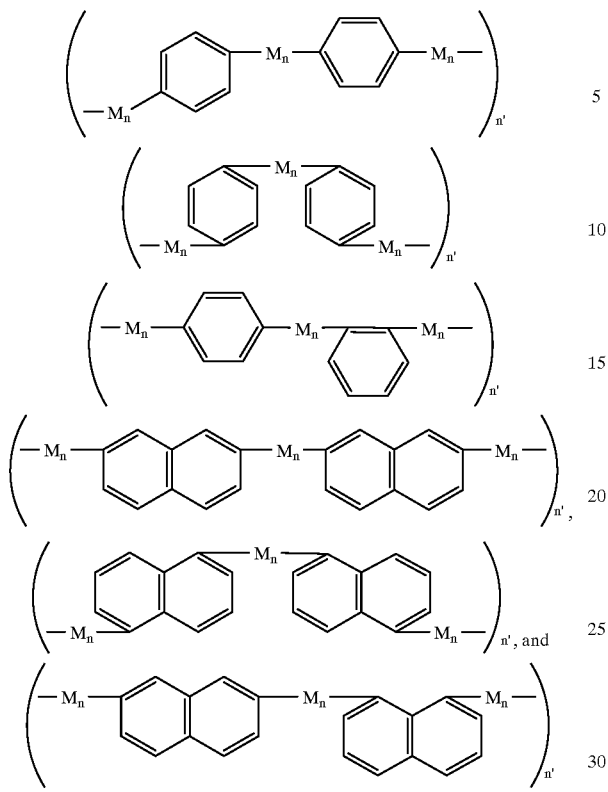

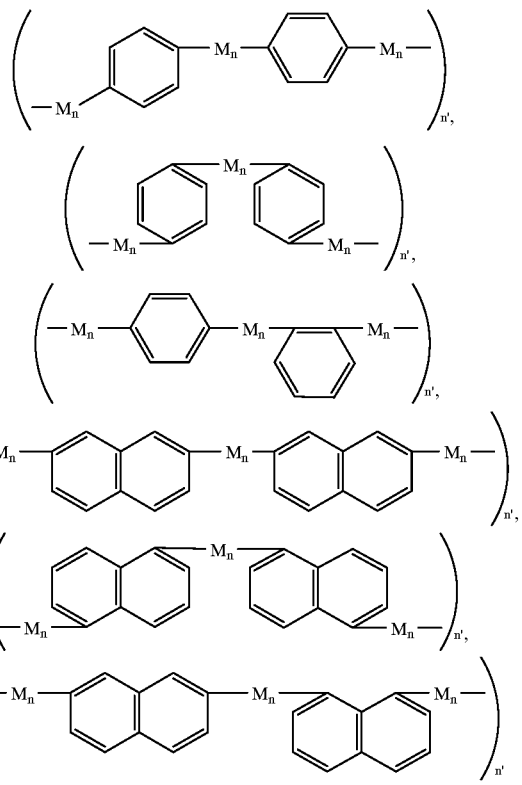

where M is an aliphatic group; and n and n' are positive integers.

3. The transplant of claim 1, wherein said aliphatic groups are selected from $CH_2$, NH, CO, and SH.

4. The transplant of claim 2, wherein said aliphatic group is selected from the group consisting of $CH_2$, NH, CO, and SH.

5. The transplant of claim 1, wherein said membrane has a porosity that permits passage therethrough of nutrients and a biological product of interest.

6. The transplant of claim 2, wherein said membrane has a porosity that permits passage therethrough of nutrients and a biological product of interest.

7. The transplant of claim 6, wherein said biological product is selected from the group consisting of insulin, dopamine, and thyroid hormone.

8. The transplant of claim 2, wherein n is a number from 1 to 8.

9. The transplant of claim 1, wherein said membrane has a porosity to moiety cell nutrients but prevent passage of immunogenic agents.

10. An artificial organ for transplantation wherein said organ is coated with a polymeric membrane, said membrane having an aromatic ring backbone with interspersing aliphatic groups wherein said membrane is not poly-para-xylylene, poly-monochloro-xylylene, and poly-dichloro-xylylene.

11. The artificial organ of claim 8, wherein said polymeric membrane comprises a structure selected from the group consisting of:

where M is an aliphatic group; and n and n' are positive integers.

12. The artificial organ of claim 10, wherein said aliphatic groups are selected from the group consisting of $CH_2$, NH, CO, and SH.

13. The artificial organ of claim 11, wherein said aliphatic group is selected from the group consisting of $CH_2$, NH, CO, and SH.

14. The artificial organ of claim 11, wherein said membrane has a porosity that permits passage therethrough of nutrients and the biological product of interest.

15. The artificial organ of claim 14, wherein said biological product is selected from the group consisting of insulin, dopamine, and thyroid hormone.

16. The artificial organ of claim 11, wherein n is a number from 1 to 8.

17. A method for protecting against biofouling of a transplant said method comprising coating said transplant with a polymeric membrane, said membrane having an aromatic ring backbone with interspersing aliphatic groups wherein said membrane is not poly-para-xylylene, poly-monochloro-xylylene, and poly-dichloro-xylylene.

18. The method of claim 17, wherein said polymeric membrane comprises a structure selected from the group consisting of:

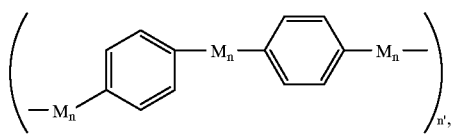

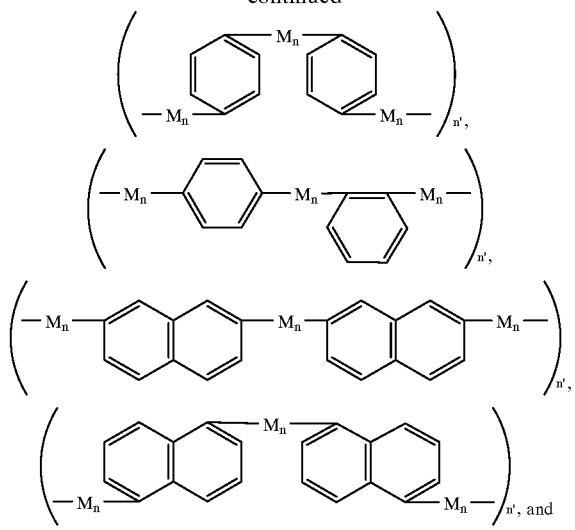

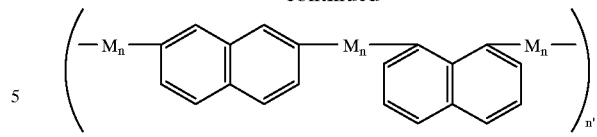

where M is an aliphatic group; and n and n' are positive integers.

19. The method of claim 18, wherein said aliphatic groups are selected from the group consisting of $CH_2$, NH, CO, and SH.

20. The method of claim 19, wherein said aliphatic group is selected from the group consisting of $CH_2$, NH, CO, and SH.

21. The method of claim 19, wherein said membrane has a porosity that permits passage therethrough of nutrients and the biological product of interest.

22. The method of claim 21, wherein said biological product is selected from the group consisting of insulin, dopamine, and thyroid hormone.

* * * * *